(12) United States Patent
Lewis

(10) Patent No.: US 7,195,908 B2
(45) Date of Patent: *Mar. 27, 2007

(54) SUPPORTS TREATED WITH TRIAMINE FOR IMMOBILIZING BIOMOLECULES

(75) Inventor: Mark A. Lewis, Corning, NY (US)

(73) Assignee: Corning Incorporated, Corning, NY (US)

( * ) Notice: Subject to any disclaimer, the term of this patent is extended or adjusted under 35 U.S.C. 154(b) by 187 days.

This patent is subject to a terminal disclaimer.

(21) Appl. No.: 10/284,762

(22) Filed: Oct. 31, 2002

(65) Prior Publication Data

US 2004/0086939 A1 May 6, 2004

(51) Int. Cl.
*C12Q 1/68* (2006.01)

(52) U.S. Cl. ............... 435/285.2; 435/6; 435/287.2; 435/287.9; 422/68.1; 430/58.75

(58) Field of Classification Search ............... 435/4, 435/6, 7.1, 7.9, 7.92, 174, 176, 287.1, 287.2, 435/9, 969, 970, 975, 285.2, 287.9; 436/164, 436/518, 524, 532, 823; 422/68.1; 430/58.75
See application file for complete search history.

(56) References Cited

U.S. PATENT DOCUMENTS

| | | | |
|---|---|---|---|
| 4,141,857 A * | 2/1979 | Levy et al. | 502/439 |
| 4,529,618 A | 7/1985 | Ponjee et al. | 427/82 |
| 4,581,336 A * | 4/1986 | Malloy et al. | 435/176 |
| 5,087,522 A | 2/1992 | Bailly et al. | 428/402 |
| 5,474,796 A | 12/1995 | Brennan | 427/2.13 |
| 5,510,270 A | 4/1996 | Fodor et al. | 436/518 |
| 5,688,642 A * | 11/1997 | Chrisey et al. | 435/6 |
| 5,728,588 A * | 3/1998 | Caldwell et al. | 436/532 |
| 5,858,653 A | 1/1999 | Duran et al. | 435/6 |
| 5,959,098 A | 9/1999 | Goldberg et al. | 536/25.3 |
| 6,159,695 A | 12/2000 | McGovern et al. | 435/6 |
| 6,548,264 B1 * | 4/2003 | Tan et al. | 435/7.21 |
| 6,750,023 B2 | 6/2004 | Tanner et al. | 435/6 |
| 2003/0054176 A1 * | 3/2003 | Pantano et al. | 428/429 |
| 2003/0059819 A1 | 3/2003 | Tzeng et al. | 435/6 |
| 2003/0099930 A1 | 5/2003 | Graves et al. | 435/5 |
| 2003/0215806 A1 | 11/2003 | Lewis | 435/6 |
| 2004/0043508 A1 | 3/2004 | Frutos et al. | 436/518 |

(Continued)

FOREIGN PATENT DOCUMENTS

WO     WO 99/57323     11/1999

(Continued)

OTHER PUBLICATIONS

Chrisey et al., "Covalent attachment of synthetic DNA to self-assembled monalayer films," Nucleic Acids Research 24:3031-3039 (1996).*

(Continued)

*Primary Examiner*—Long V. Le
*Assistant Examiner*—Christine Foster
(74) *Attorney, Agent, or Firm*—Lawrence A. Villanueva; Thomas R. Beall

(57) ABSTRACT

Supports for immobilizing molecules, particularly biomolecules, methods of making such supports, kits, and biomolecular hybridization assay devices are disclosed. The methods, supports and devices include forming a triamine layer on at least a portion of a substrate and attaching a compound to a portion of the substrate.

20 Claims, 2 Drawing Sheets

U.S. PATENT DOCUMENTS

2004/0076961 A1* 4/2004 Lewis ........................... 435/6
2004/0086939 A1 5/2004 Hancock et al. ............. 435/7.1
2004/0146460 A1* 7/2004 Salafsky ..................... 424/9.6

FOREIGN PATENT DOCUMENTS

WO     WO 00/18957    *   4/2000

OTHER PUBLICATIONS

Voet & Voet, Biochemistry, 1995, 2nd Edition, John Wiley & Sons, Inc., p. 175.*

Qhobosheane et al. "Biochemically functionalized silica nanoparticles" Analyst (published online Jul. 20, 2001) vol. 126, p. 1274-1278.*

Pierce Biotechnology Inc. Instructions: SMCC and Sulfo-SMCC, Product Nos. 22360 and 22322, Nov. 2005, downloaded from www.piercenet.com on Oct. 12, 2006.*

Kazuyuki Hayashi et al., "Regulation of the Surface Potential of Silicon Substrates in Micrometer Scale with Organosilane Self-Assembled Monolayers", Langmuir 2002, vol. 18, pp. 7469-7472.

U.S. Appl. No. 11/027,318, filed Dec. 30, 2004, Mark A. Lewis.

* cited by examiner

SUPPORTS TREATED WITH TRIAMINE FOR IMMOBILIZING BIOMOLECULES

FIELD OF THE INVENTION

This invention relates to supports used for immobilizing biomolecules and methods of making such supports. More particularly, the present invention relates to supports having a triamine surface treatment and methods of fabricating such treated supports.

BACKGROUND OF THE INVENTION

Analysis of the structure, organization and sequence of nucleic acid molecules is important in the prediction, diagnosis and treatment of human disease and in the study of gene discovery, expression and development. One laboratory tool used in the analysis of nucleic acid molecules is the high density array (HDA). The HDA provides the framework for immobilization of biomolecules such as nucleic acid molecules for analysis on a rapid, large-scale basis. HDAs generally include a substrate having a large number of positionally distinct DNA probes attached to a surface of the substrate for subsequent hybridization to a DNA target.

The surfaces of both organic and inorganic substrates can be modified by the deposition of a polymeric monolayer coating or film to construct biomolecular assemblies. In addition, surface modification can also be used to promote adhesion and lubrication, modify the electrical and optical properties of the substrate surface, and create electroactive films suitable for various optical and electronic sensors and devices.

Compounds with amine functionality have been used in the preparation of surfaces for nucleic acid hybridization. Due to their ability to bond to a substrate with a hydroxyl group and their ability to bond to nucleic acids through an amine, silane compounds are useful as surface coatings that will effectively immobilize nucleic acids. One example of a silane used for biological assay preparation is gamma amino propyl silane (GAPS), which may be deposited by a variety of methods, including but not limited to, spin coating, spray coating and dip coating. GAPS slides provide a surface that immobilizes DNA through the non-covalent, electrostatic attachment to the slide surface. The GAPS molecule contains a single amine functionality and has a 3 carbon linker between the Si and the amine.

A very important consideration in the preparation of substrates for immobilization of biomolecules is uniformity of the substrate surface. It is important to provide uniform functionality over an extended area of the substrate. This is especially true in the case of high density arrays for performing biomolecular hybridization assays. Such assays rely on having uniform levels of biomolecule immobilization at known locations on the substrate. It is desirable to have substantially identically sized spots containing a known quantity of pre-determined set of capture biomolecules located on the substrate in a regular geometric array with low background or signal to noise. Ambiguous and/or erroneous readouts result from variations in the immobilization and localization of the capture biomolecules.

Although GAPS coated slides are widely used for the immobilization of biomolecules, it would be desirable to provide substrates with alternate surface modifications. It would be useful to provide substrate surface adapted for immobilization of biomolecules that could be modified to provide a wide variety of surface functionalities to provide flexibility in binding various biomolecules.

SUMMARY OF INVENTION

The invention generally provides supports, methods of forming supports, kits and devices utilizing supports that include a triamine layer attached to at least a portion of a substrate surface. In certain embodiments, the triamine layer is modified by second compound. It is to be understood that both the foregoing general description and the following detailed description are exemplary and are intended to provide further explanation of the invention as claimed.

DETAILED DESCRIPTION

Figure 1:
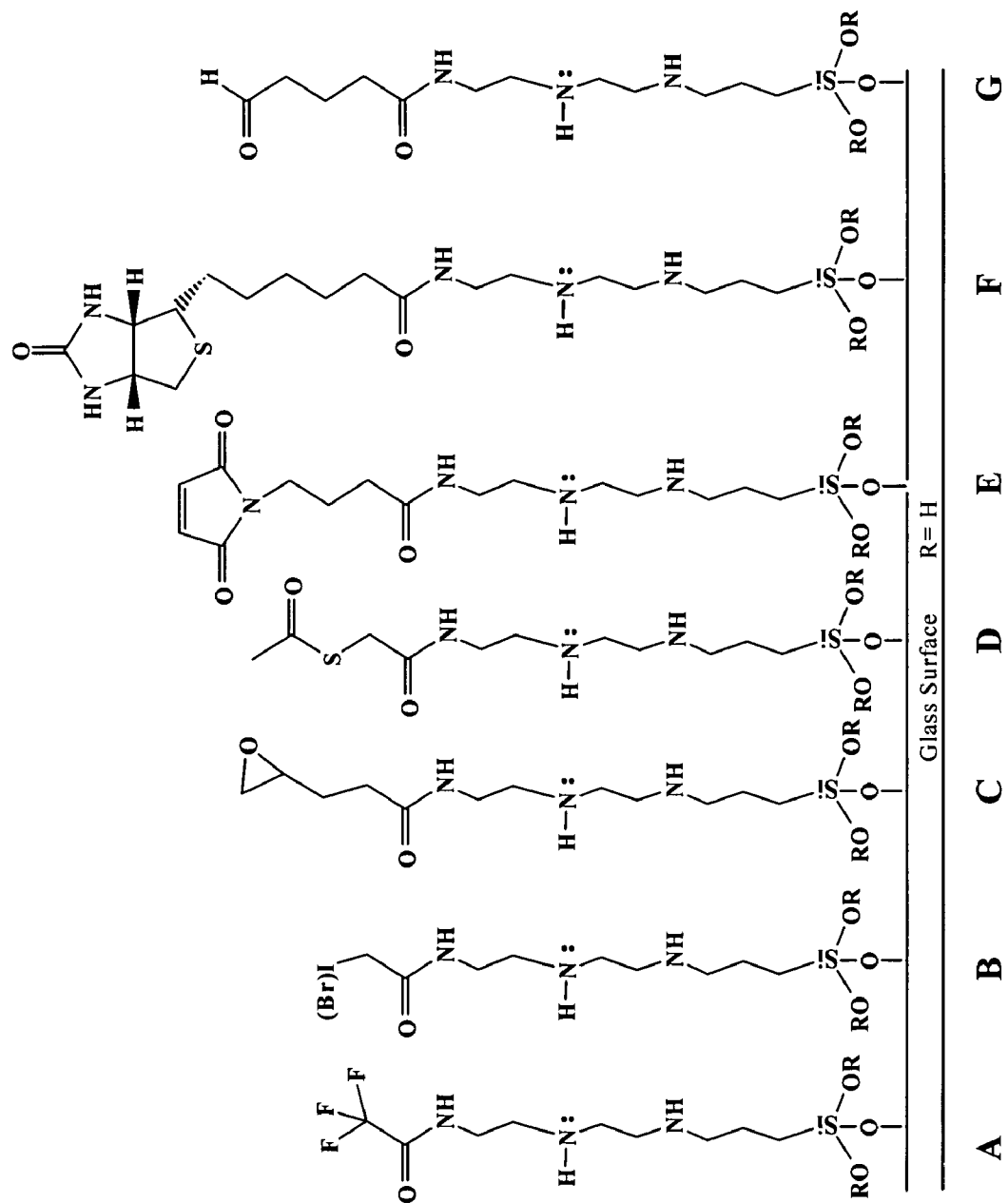
FIG. 1 is a chemical representation of various chemistries that can be attached to supports having a triamine surface layer.

In overview, certain embodiments of the present invention provide supports for immobilizing biomolecules. Other embodiments relate to methods of forming such supports, and still other embodiments relate to kits and devices utilizing such supports. Typically, the support includes a substrate such as a glass slide, but other types of supports are within the scope of the invention.

Experiments were conducted in an effort to improve biomolecule retention of DNA and increase the signal to noise readings from GAPS coated slides by adding more primary amines in an effort to increase the surface charge density. The results of these experiments gave little to no improvement. Applicants discovered that substrates including a coating or layer of a triamine provided a slide that exhibited better retention and improved signal to noise readings. The results from triamine-coated slides were also more reproducible than with GAPS-coated slides, and the slides including a triamine surface layer can be further derivatized with other compounds to generate supports with virtually any surface functionality for bonding to a wide variety of molecules.

Certain embodiments of the invention relate to a biomolecular immobilization support comprising a substrate having a surface, a triamine layer attached to the substrate surface, and a chemical compound bound to the triamine layer. According to certain embodiments, the chemical compound includes multiple functionalities. According to some embodiments, the chemical compound is bifunctional, and in some embodiments the compound is heterobifunctional. In some embodiments, the compound bound to the triamine is homobifunctional. According to some embodiments, the compound is adapted to covalently bind biomolecules, and in other embodiments, the compound is adapted to non-covalently bind biomolecules. According to some embodiments, triamine-coated substrates modified with a hydrophobic compound exhibit a water contact angle exceeding 60 degrees, and in some embodiments, the substrate exhibits a water contact angle exceeding 70 degrees. It will be understood that the triamine surface can also be modified with a hydrophilic compound to lower the water contact of the substrate to less than 38 degrees. Experiments have shown that triamine coated and modified substrates can exhibit water contact angles as low as about 30 degrees.

The triamine compounds and compounds attached to the triamine can be applied to the substrate by conventional methods such as spraying, dipping, coating, brushing and other methods that can form a uniform and reproducible coating or layer on a substrate used for immobilizing biomolecules, such as high density arrays and microplates, which can be made from a variety of materials. Such substrate materials include, but are not limited to glass, quartz or silica.

Suitable substrates for this invention are those having a surface that is accessible to solvents. The substrate itself may take any shape including, but not limited to, rectangular, square, circular, cylindrical, conical, planar and spherical. The interior surface of a bottle or tubing could be used as a substrate. The preferred substrate has a planar shape, and may be formed into a variety of HDAs, microplates and laboratory dishes.

For optical or electrical areas of application, the substrate can be transparent, impermeable or reflecting, as well as electrically conducting, semiconducting or insulating. For biological applications, the substrate material may be either porous or nonporous and may be selected from either organic or inorganic materials.

Inorganic substrate materials can include metals, semiconductor materials, glass and ceramic materials. Examples of metals that can be used as substrate materials are gold, platinum, nickel, palladium, aluminum, chromium, steel and gallium arsenide. Semiconductor materials used for the substrate material can include silicon and germanium. Glass and ceramic materials used for the substrate material can include quartz, glass, porcelain, alkaline earth aluminoborosilicate glass and other mixed oxides. Further examples of inorganic substrate materials include graphite, zinc selenide, mica, silica, lithium niobate, and inorganic single crystal materials.

Organic substrate materials are typically made from polymer materials, due to their dimensional stability and resistance to solvents. Examples of organic substrate materials are polyesters, such as polyethylene terephthalate, and polybutylene terephthalate, polyvinylchloride, polyvinylidene fluoride, polytetrafluoroethylene, polycarbonate, polyamide, poly(meth)acrylate, polystyrene, polyethylene or ethylene/vinyl acetate copolymer.

Once a suitable substrate is obtained, a triamine layer is formed on the surface of the substrate by using various techniques. A simple method of forming a layer is by dipping the substrate in an aqueous solution containing triamine silane.

Other embodiments of the invention relate to methods of preparing a biomolecular immobilization support comprising providing a substrate having a surface, attaching a triamine layer to the surface, and attaching chemical compound to the triamine layer, the chemical compound adapted to accept biomolecules. Still other embodiments of the invention relate to kits for immobilizing biomolecules comprising a substrate having a surface layer of a triamine thereon and a modifying compound adapted to be attached to the triamine layer.

Preferred triamines for forming a triamine coating or layer are triamine silanes, and particularly preferred are trialkoxy triamine silanes. According to certain embodiments, a triamine surface was generated using the commercially available $N^1$-[3-(Trimethoxysilyl)propyl]diethylenetriamine.

Examples of compounds that can be attached to the triamine layer include reactive ester compounds, trifluoroacetylated compounds, α-haloacetylated compounds, epoxy compounds, protected thiol compounds, maleimide compounds, biotinylated compounds, and aldehyde compounds. FIG. 1 shows a chemical representation of a substrate 10 coated with a triamine layer 12. As shown in FIG. 1, the triamine layer is a trialkoxy triamine silane. The triamine surface layer can be derivatized with a wide variety of compounds. FIG. 1 shows a single slide coated with a triamine and modified with various functional groups. It will be understood that typically, a single slide coated with a triamine will be modified with a single compound and not with multiple compounds as shown in FIG. 1. FIG. 1 shows multiple compounds to give examples of the variety of surfaces that can be provided according to certain embodiments of the present invention. For example, in column A, the triamine is modified with a trifluoroacetyl compound. In column B of FIG. 1, the triamine is modified with an α-haloacetyl compound, and in column C, the triamine is modified with an epoxy compound. In column D of FIG. 1, the triamine is modified with a protected thiol group, and in column E, the triamine is modified with a maleimide compound. In column F of FIG. 1, the triamine layer has been biotinylated, and in column G, the triamine layer has been modified with an aldehyde. The modifications shown in FIG. 1 represent a small number of modifications possible to enable the attachment of proteins or other target molecules to a substrate having a triamine layer attached thereto. Those skilled in the art will appreciate that a wide variety of multifunctional or bifunctional groups can be attached to the triamine layer to enable of the attachment of various molecules to the substrate. Virtually any electrophilic, nucleophilic or ionic groups can be attached to the triamine layer to provide the desired attachment chemistry.

Figure 2:
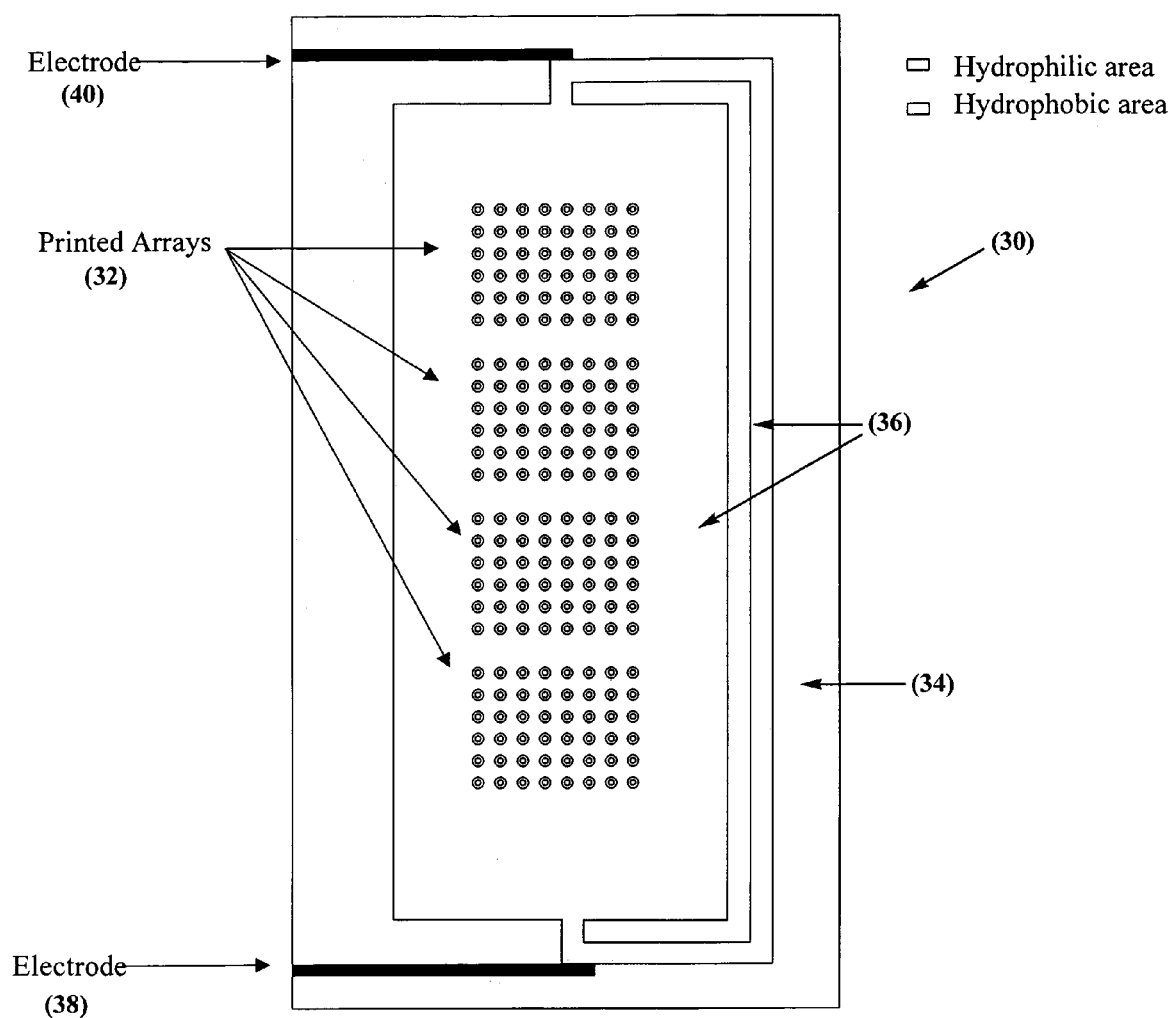
FIG. 2 is a schematic representation showing a biomolecular assay device according to one embodiment of the invention.

According to certain embodiments of the invention, biomolecular assay devices can be manufactured by providing a substrate having a surface and providing a pattern of hydrophobic and hydrophilic regions on the surface of the substrate. In preferred embodiments, the hydrophilic and hydrophobic regions are formed in a pattern by selectively depositing chemical compounds on selected regions of the substrate surface. According to certain embodiments, a triamine layer can be formed on at least a portion of the substrate surface, preferably in a pattern, and then, at least one compound can be attached to the triamine layer on selected regions of the substrate, preferably in the form of a pattern. In certain preferred embodiments, the triamine layer and the compound attached at selected regions form a pattern to provide hydrophilic and hydrophobic regions on the surface of the substrate. According to certain embodiments, the pattern is in the form of at least one continuous channel to provide for flow across the surface of the substrate. It may further be desirable to provide electrodes for providing electroosmotic or electrophoretic flow of fluids on the substrate surface. FIG. 2 shows an example of a biomolecular assay device 30, including a surface with printed arrays 32 thereon. The device 30 further includes a hydrophobic area 34 and a hydrophilic area 36, which can be provided by forming hydrophilic and hydrophobic layers in the desired areas. In the embodiment shown in FIG. 2, the hydrophilic area 36 is in the form of a channel connected to electrodes 38 and 40. The electrodes can be utilized to provide electroosmotic or electrophoretic fluid flow to the printed arrays 32. One way of generating a pattern of hydrophobic and hydrophilic regions according to certain embodiments of the invention could include providing a substrate modified with a triamine layer. The triamine layer could then be selectively modified using soft lithography techniques such as soft contact printing or masking and photolithography. The unmodified triamine area would provide a hydrophilic region, while the modified region could be modified with a hydrophobic compound such as an alkane NHS ester. In certain embodiments, probes or molecules would be printed on the hydrophilic areas. It will be understood that FIG. 2 depicts only one pattern, and a wide variety of patterns could be generated according to the present invention. A chemically modified, patterned fluid chamber could eliminate the need for complex hybridization chambers that require mechanical pumping.

According to certain embodiments of the invention, DNA or oligonucleotides are attached to the coated substrates. Other biological or synthetic molecules can be attached to the coated substrate. For example, other synthetic molecules include, but are not limited to, ribonucleic acids (RNA), deoxyribonucleic acids (DNA), synthetic oligonucleotides, antibodies, proteins, peptides, lectins, modified polysaccharides, synthetic composite macromolecules, functionalized nanostructures, synthetic polymers, modified/blocked nucleotides/nucleosides, modified/blocked amino acids, fluorophores, chromophores, ligands, chelates, and haptens.

Various techniques are known in the art for immobilizing DNA and oligonucleotides on surfaces, essentially any of which can be used in the practice of the invention. A discussion of representative immobilization techniques used in the art can be found in U.S. Pat. No. 5,919,626 and the references listed in that patent. Similarly, immobilization techniques are known for other biomolecules, such as specific binding members. Along the same lines, techniques for immobilization of molecules useful in tissue culture systems, e.g., collagen, are also well-known in the art. It is understood that surfaces produced in accordance with the present invention can be used to immobilize a variety of biomolecules including, but not limited to DNA arrays, oligonucleotides, protein arrays and cell arrays.

The natural evolution of the high density arrays is to put as much genomic information on a single slide as possible, the entire human genome for example. To achieve this goal, the surface would need to be more hydrophobic so that the diameter of the spots, as well as the spot spacing, could be decreased to accommodate the entire genomic array. GAPS slides can be driven to contact angles as high as 80–90 degrees through heat treatments. This result, however, is not very reproducible.

According to certain embodiments of the invention, reproducible surfaces exhibiting a higher contact angle surface capable of binding DNA were designed. Since the triamine is a linear triamine compound with the capability of multiple bonding modes, it was envisioned that reacting the primary amine with the proper reagent would give the desired result. Many different amine alkylating, acylating and acetylating reagents can be used for the purpose of modifying the primary amine of the triamine surface and the water contact angle of the substrate surface.

While the present invention should not be limited by a particular theory, one idea behind the use of a triamine surface as an alternative to the current GAPS surface was based on the desire to obtain a higher signal to noise of the resultant hybridization signal. The current use of GAPS utilizes the primary amino functionality due to its ability to protonate in buffered neutral water (pKa~10) to give a positive charge (ammonium ion). With the DNA molecule having a net negative charge, due to the phosphate backbone, under the right conditions an electrostatic (ionic) bond can be formed between the surface ammonium ions and the DNA allowing for immobilization. The formation of the ionic bond can be illustrated as simply the reverse of the salvation process.

The salvation process can be illustrated stepwise with the solvent eventually forming a cage around each ion giving the solvated ions. The reverse of this process is the stepwise formation of the ionic bond. The key to the formation of an ionic bond is the complete removal of the intervening solvent. If there is any residual solvent separating the ions, a tight ion pair cannot be formed. In the instance of the interaction between the DNA and the surface, if the solvent is not removed completely, the DNA will not be tightly bound and could very well come off the surface during post-print processes. Another effect would be that the printed DNA would have a degree of surface mobility leading to observations of spot merging and/or smearing and cometing. This is important since the interaction of the DNA with the GAPS surface is a single point of contact per molecule of silane. That is, for every primary ammonium ion on the surface, one phosphate of the DNA backbone has the potential to form one ionic bond. A decrease in the number of contact points on the surface reduces its capability to effectively immobilize DNA and leads directly to the loss of material from the surface.

Each GAPS molecule, as stated above, is a single primary amine which upon protonation leads to the positively charged ammonium ion. The surface generated by a primary amine silane therefore can only have one ionic bond per molecule. If the efficiency of biomolecular immobilization of a particular surface chemistry is defined by the charge density, then GAPS would have a value of 1 (amine/molecule). If the degree of immobilization is a function of the charge density, then it follows that an increase in the number of binding sites per molecule will give greater immobilization or better retention. In the case of amines, forming positively charged ammonium ions on exposure to neutral water, increasing the number of amines per molecule would increase the overall charge density limited by, of course, space charge effects. That is, since positive charges repel each other, only a certain number of them can occupy a fixed volume, which translates to the fact that all amines will not be protonated. In light of this fact, it becomes obvious that one should not be limited to ionic bonds as the only means of non-covalent interactions for biomolecular immobilization.

Other non-covalent interactions such as Van DerWaals, dipole-dipole, and hydrogen bonding should also be considered in concert with the ionic interaction when considering new surface molecules for biomolecular immobilization. The inclusion of these other modes of binding would mean that the efficiency of biomolecular immobilization is more than the charge density. A true measure would have to be the sum of the charge density and all other modes combined to give a value defined as the bond density. In its simplest form, increasing the bond density from 1 to 2 to 3 would mean going from GAPS to diamine to triamine. With triamine, the DNA is not restricted to a single ionic interaction, but may also form hydrogen bonds with the polyamino triamine derivatized surface. An amine moiety can be protonated to give a positive charge, and it can also function as a hydrogen bond donor as well as acceptor. An increase in the number of amines per silane molecule is just one way to increase the bond density. Groups that have a strong dipole or aromatic rings are just a few other moieties that could also be beneficial. The bottom line is that the individual DNA strands have the capability to form more than one bond per molecule and will therefore allow for a stronger interaction with the surface. This strong interaction with the polyamino surface then translates to better retention and greater hybridization signal.

Another key issue governing the performance of an organic coating on glass slides is the thickness of the deposited layer. It has been thought that the GAPS silane does not give a monolayer due in part to the 3 carbon atom spacer between the Si and amine. In other words, the Self Assembled Monolayer (SAM) phenomenon does not actively occur until chain lengths of $C_8$ or greater. This then accounts for the multi layer composition of the GAPS surface measured to around 10 Angstroms. With the triamine surface, having a 9 atom spacer between the Si and amine, it would be more likely give a monolayer.

Without intending to limit the invention in any manner, the present invention will be more fully described by the following examples.

EXAMPLES

Materials

The solvents used (THF, Hexane) were purchased in SureSeal bottles and were used without further purification. Other reagents used such as methanol, ethanol, acetone were purchased and used without further purification. All reagents (Silane) used for surface chemistry were purchased from United Chemical Technologies (UCT) or Gelest and used without further purification. All the glassware used in the surface modifications was cleaned with soap, rinsed with tap water, rinsed with DI water and then rinsed with acetone and placed in the drying oven at 100° C.

Pre-treatment

All the slides were subjected to a pre-treatment prior to surface modification with the trialkoxysilane $N^1$-[3-(Trimethoxysilyl)propyl]diethylenetriamine. Because the slides have a non-uniform distribution of surface hydroxyls as well as possible organic contaminants, the slides were put in a staining dish that contained 4N NaOH and were stirred for 1 hour at room temperature. The slides were then removed from the hydroxide solution and dipped into a beaker containing DI water. The slide was agitated for a few seconds then rinsed with methanol (ethanol). This process was repeated twice. Once all the slides had been washed and rinsed and placed into a clean staining dish, they were put into the oven at 100° C. until needed for the next step. Before silane deposition, the slides were treated with oxygen plasma at 200 Watts for 10–15 minutes.

Methods-Dry Box

Due to the reactive nature of the chemicals used and their susceptibility to hydrolysis, the initial reactions were carried out in a dry box with all glassware cleaned and dried prior to insertion into the anti-chamber. The protocol for silane deposition for all of the later experiments used an aqueous ethanol procedure taken from the United Chemical Technologies (UCT) catalog. Briefly, the procedure consisted of making a 2–5% silane solution in 95:5 ethanol/water and allowing this to stir for 5 minutes to effect silane hydrolysis. The pre-treated slides were then exposed to this solution for 2–5 minutes at which time the slides were removed, rinsed with ethanol, rinsed with water and again with ethanol. The slides were then placed in the oven (100° C.) for 30 minutes. The slides were removed from the oven and kept covered until needed.

Methods—Moisture Sensitive Procedure

Since the alkoxysilane hydrolysis takes place in the presence of air, all the surface chemistry was done in a Dry Box (moisture free). The reagents were pumped into the dry box using 3 cycles of pump and back filling with 99.9999% Ar. The glassware needed for a surface chemistry reaction was taken directly from the oven and placed into the anti-chamber. Once all the glassware (including the pre-cleaned slides) was put into the anti-chamber, it was immediately pumped down to remove the air introduced during the loading of the chamber. If the contents of the chamber contained no sealed containers, the chamber was fully pumped down. If, on the other hand, there were closed containers (as is the case when bringing silane reagent bottles into the box) then the chamber is not pumped down completely and instead of 3 pump cycles there are 4 to 5. This is to prevent the bottles from breaking from the pressure differential. Once everything needed for the experiment was in the box, the solution was made in a volumetric flask and then subsequently added to the staining dish containing the slides. The cover was put on the dish and the contents allowed to stir for 1 hour in the dry box. After one hour, the dish was removed from the dry box and placed in the fume hood and stirred for an additional 15 minutes. The stirring was then stopped and each slide was removed and rinsed with ethanol into a waste jar and then dipped into a beaker containing DI water. The slide was swirled around and the cycle repeated. After the final ethanol wash the slides were placed into a clean staining dish without drying with $N_2$. Once all the slides had been cleaned and placed in the dish, the entire dish (plus lid) was placed in the drying oven (at 100° C.) for 30 minutes. After the 30 minutes the lid was placed on the dish and removed from the oven and placed on the counter to cool.

Instrumentation

The DNA was printed using the Cartesian Technologies printer and the associated software package. A quill pin was used to print the arrays. Before each group of slides was printed the pin was sonicated in Arrayit micro cleaning solution for 5 minutes followed by isopropanol for 5 minutes. The arrays were visualized using the General Scanner ScanArray 3000 system. This system has the lasers (2) tuned for Cy 3 and Cy 5 fluorescent dyes.

DNA Protocol

The surface was printed with a 10×10 array of spots using the 1.5 Kb double stranded DNA PCR product (pBR322; pst I to sal I vector) at 100 nmol/uL (~100 ng/uL). The slides were then incubated at 100° C. for 4 hours. The slides were then pre-hybridized for 45 minutes in a solution containing 25% formamide, 5×SSC, 0.1% SDS that has been warmed to 42° C. If necessary, 1% bovine serum albumin (BSA) can be added for blocking. The slides were rinsed under running distilled water and isopropanol and dried with nitrogen, placed in boiling water for 2 minutes, rinsed with isopropanol and dried with nitrogen, and put into hybridization chamber (Corning hybridization chamber) with 20–40 uL water for humidity. 20 uL probe DNA (0.01 pmol/uL in hybridization buffer) was added to the hybridization chamber and a cover slip was slowly dropped into place. The hybridization chamber was sealed and put in water bath at 42° C. to hybridize overnight.

After overnight hybridization, the slide with cover slip was placed in large volume 2×SSC/0.1% SDS at 42° C., and the cover slip was allowed to come off. The slide was then treated with 200 ml of 2×SSC/0.1% SDS (5 min 42° C.), 0.1×SSC/0.1% SDS at room temp (10 min), 0.1×SSC (1 minute; 4 repeats), rinsed with running distilled water less than 10 seconds, rinsed with ETOH and dried with nitrogen.

Results and Discussion

Example 1

Triamine Coated Slides Printed with DNA

Surfaces were deposited on glass slides as described above, printed with labeled DNA, scanned, treated (depending on the nature of the ink used), boiled in water for 2 minutes and re-scanned. A successful surface candidate had a high retention of DNA as determined by the ratio of the fluorescence signal before and after boiling. Visual inspection of slides determined that triamine coated slides provided a surface with printed spots that did not give "comets" and there is little to no background interference. The triamine surface binds DNA very well and is a very good surface for DNA (or biomolecular) immobilization.

Example 2

Surface Analysis

The DNA experiments showed the triamine-modified substrate surface to be a strong candidate as suitable surface for DNA arrays. It had been shown in previous experiments that the GAPS slides had white globules (oligomers of GAPS) randomly distributed on the surface that could be washed off in water. In the absence of the washing, however, the globules remained give a less than smooth surface texture. AFM analysis for both triamine and a GAPS coated surfaces determined that the triamine surface has a much smoother appearance and an obvious absence of white globules clearly seen on the GAPS slide. The white globules on the GAPS image have been shown by further analysis to be oligomers of the GAPS monomer. The surface analysis of the triamine has shown it to be an extremely smooth surface as judged by AFM. The use of an ellipsometric method utilizing a silicon substrate gave good numbers indicating that a good monolayer is being deposited. The monolayer deposition translates to a more well behaved and predictable system. That is, the surface is relatively uniform with the primary amines of the triamine molecule being presented to the printed DNA. Initial boil tests have shown the surface to be quite durable with a high degree of biomolecular immobilization as shown through good DNA retention. A true test of the triamine surface, of course, lies in the direct evaluation to the GAPS surface through a side-by-side comparison study.

Example 3

Comparison of Triamine Slides with GAPS Slides

The next step in the evaluation of the triamine surface as a surface for HDA applications was to do a side-by-side comparison to the GAPS surface. Corning GAPS slides were obtained and triamine slides were prepared. The standard printing and hybridization protocols were followed and these are outlined in detail in the methods section above. Each surface chemistry was done in triplicate for the purpose of generating statistically significant data. A total of 6 six slides (3 triamine and 3 CMT GAPS) were run together. Visual inspection of the slides showed that the signal from the triamine slides is significantly greater than that of the signal from the GAPS slides. The spot morphology and overall background of the triamine slides were very good. The target DNA (printed) and the probe DNA (hybridization solution) were labeled in order to evaluate the surface performance. The target DNA provides for a measure of the retention after 2 minutes in boiling water. The probe DNA was used to measure the hybridization information. To get the numbers for each of the metrics, the respective scans were analyzed using Corning's GridGrinder array analysis software.

Since the array was printed with labeled DNA, the amount of DNA retained could be determined as a percentage of the original material printed. The average signal to background (S/B) of the triamine surface was 160 versus the GAPS surface S/B of 26. This constitutes an increase in signal intensity of greater than 6 times compared to the GAPS. It is also interesting to note that the amount of DNA remaining on the triamine slide after the 2 minutes in boiling water was approximately 3 times that of the DNA on the GAPS slides. The increase in the retention of the DNA illustrates the enhanced capability of the triamine surface to bind the DNA through the multiple modes of attachment.

Example 4

Engineered Surfaces and Contact Angle Modification

Since the triamine is a linear triamine compound with the capability of multiple bonding modes, it was envisioned that reacting the primary amine with the proper reagent would give the desired result. Many different amine alkylating, acylating and acetylating reagents were considered for the purpose of modifying the primary amine of the triamine surface. For ease of application, acid chlorides and anhydrides were considered first. One proper reagent for the end capping of the triamine was trifluoroacetic anhydride (TFAA). This particular reagent was chosen because the trifluoro group would give a surface that would be very low in free energy, thus giving a more hydrophobic surface. Triamine coated slides were treated with a dilute solution of TFAA in anhydrous tetrahydrofuran (THF) for 30 minutes. The slides were removed and the excess material rinsed off and the slides blown dry with nitrogen. To check on the effect of this primary amine surface modification, before and after treatment water contact angles were taken. The table below shows a few of the slides water contact angles before and after, with the average increase of about 35°. This was extremely encouraging since the same experiment run on CMT GAPS slides (data not shown) gave only an average increase in water contact angle of approximately 4°. This data also gives a strong indicator for the number of amines on any given amino terminated surface. That is, the greater the increase in the water contact angle after treatment with TFAA of a given amine terminated surface, the greater the number of amines that are present on the surface.

If the initial hypothesis is true and the silane surface still has the secondary amines, or two bonding modes per molecule left, DNA should still be retained by the surface. To investigate this, the TFAA capped triamine surface was printed with the 1.5 Kb DNA, scanned, cured and then boiled in water and re-scanned. Visual inspection of the slides showed that the TFAA capped surface retains the ability to bind DNA quite strongly. The spot diameter (roughly 120 microns) was reduced as a result of the TFAA termination of the surface. Some of the spots on the slide after boiling do show a minor amount of smearing but this can be easily solved through the use of a blocking agent in the prehybridization solution. In one type of prehybridization solution there is 1% BSA as a blocking agent to prevent DNA that has come off the surface from re-attaching. Hybridization using a prehybridization solution and a TFAA capped slide provided good overall hybridization signal.

| Slide Number | Contact Angle | Change in CA |
|---|---|---|
| Slide #511 -- Triamine | 40.8 | 31.0 |
| Slide #511 -- modified with TFAA | 71.8 | |
| Slide #512 -- Triamine | 39.9 | 34.0 |
| Slide #512 -- modified with TFAA | 73.9 | |
| Slide #513 -- Triamine | 41.2 | 35.2 |
| Slide #513 -- modified with TFAA | 76.4 | |
| Slide #514 -- Triamine | 38.0 | 35.9 |
| Slide #514 -- modified with TFAA | 73.9 | |

DNA arrays are expected to contain a greater density of spots, and with the possibility of a complete human genome chip, the surface of substrates will need to be extremely hydrophobic yet have the ability to strongly bind the DNA. It has been shown that the triamine can be modified at its terminal primary amine function with the binding capability carried out by the remaining two secondary amines per molecule. A trifluoroacetylated triamine is just one example of an engineered surface that was hydrophobic in a controlled manner yet maintained the electrostatic binding capacity. It will be apparent to those skilled in the art that various modifications and variations can be made to the present invention without departing from the spirit or scope of the invention. For example, a variety of triamine compounds and modification compounds containing various functional groups appropriate for biomolecule immobilization may be used in accordance with the present invention. Thus, it is intended that the present invention cover modifications and variations of this invention provided they come within the scope of the appended claims and their equivalents.

What is claimed is:

1. A biomolecular immobilization support for immobilizing a biomolecule comprising a substrate having a surface, a triamine layer covalently attached to the substrate surface, and a trifluoroacetyl group bound to the triamine layer, wherein the triamine layer non-covalently binds to the biomolecule, and wherein the trifluoroacetyl group increases the water contact angle of the substrate to greater than 60 degrees.

2. The support of claim 1, wherein the water contact angle exceeds 70 degrees.

3. The support of claim 1, wherein the triamine layer includes a triamine silane.

4. The support of claim 3, wherein the triamine layer includes a trialkoxy triamine silane.

5. A method of preparing a biomolecular immobilization support for immobilizing a biomolecule comprising: providing a substrate having a surface; covalently attaching a triamine layer to the surface; and attaching a trifluoroacetyl group to the triamine layer, the triamine layer capable of non-covalently binding to the biomolecule, wherein the trifluoroacetyl group increases the water contact angle of the substrate to greater than 60 degrees.

6. The method of claim 5, wherein the triamine layer is provided by coating the substrate with a triamine silane compound.

7. The method of claim 6, wherein the triamine silane compound includes a trialkoxy triamine silane.

8. A biomolecular assay device comprising the support of claim 1, wherein the substrate comprises a plurality of regions and wherein the triamine layer and the trifluoroacetyl group bound thereto are attached on selected regions of the plurality of regions of the substrate.

9. The device of claim 8, wherein the selected regions form a pattern.

10. The device of claim 9, wherein the pattern includes hydrophilic and hydrophobic regions.

11. The device of claim 10, wherein the pattern is in the form of at least one continuous channel to provide for flow across the surface of the substrate.

12. The device of claim 11, further comprising electrodes for providing electroosmotic or electrophoretic flow of fluids on the substrate surface.

13. A method of manufacturing the biomolecular assay device of claim 8, comprising:
    covalently attaching the triamine layer to the selected regions of the substrate to provide a pattern on the surface of the substrate; and attaching the trifluoroacetyl group to the triamine layer.

14. The method of claim 13, wherein the pattern is in the form of a channel.

15. The method of claim 14, further comprising providing hydrophilic and hydrophobic regions on the substrate surface.

16. The method of claim 13, further comprising providing electrodes associated with the device.

17. The method of claim 16, wherein the electrodes are operative to provide electrophoretic and electroosmotic flow.

18. The support of claim 1, wherein the substrate includes an inorganic material.

19. The support of claim 18, wherein the inorganic material is a metal, a semiconductor material, or ceramic material.

20. The support of claim 18, wherein the inorganic material is glass.

* * * * *